United States Patent
Babcock et al.

(10) Patent No.: US 11,278,603 B2
(45) Date of Patent: Mar. 22, 2022

(54) ENZYME COMPOSITIONS WITH REDUCED VIRAL AND MICROBIAL CONTAMINATION

(71) Applicant: AbbVie Inc., North Chicago, IL (US)

(72) Inventors: Martin Babcock, Pleasant Prairie, WI (US); Cynthia Burnell, Gurnee, IL (US); Vikram Kalthod, Mattawan, MI (US); Joerg Breitenbach, Wiesbaden (DE); Frithjof Sczesny, Hannover (DE); Frauke-Regina Rueffer, Hannover (DE); George Shlieout, Hannover (DE)

(73) Assignee: AbbVie Inc., North Chicago, IL (US)

( * ) Notice: Subject to any disclaimer, the term of this patent is extended or adjusted under 35 U.S.C. 154(b) by 73 days.

(21) Appl. No.: 15/717,396

(22) Filed: Sep. 27, 2017

(65) Prior Publication Data
US 2018/0036393 A1    Feb. 8, 2018

Related U.S. Application Data

(63) Continuation-in-part of application No. 15/470,386, filed on Mar. 27, 2017, now abandoned.

(60) Provisional application No. 62/454,184, filed on Feb. 3, 2017, provisional application No. 62/452,746, filed on Jan. 31, 2017, provisional application No. 62/314,048, filed on Mar. 28, 2016.

(51) Int. Cl.
| | |
|---|---|
| *A61K 38/54* | (2006.01) |
| *C12N 9/94* | (2006.01) |
| *A61K 38/46* | (2006.01) |
| *A61L 2/08* | (2006.01) |
| *C12N 9/20* | (2006.01) |
| *C12N 13/00* | (2006.01) |
| *A61K 41/10* | (2020.01) |

(52) U.S. Cl.
CPC ............ *A61K 38/54* (2013.01); *A61K 38/465* (2013.01); *A61K 41/10* (2020.01); *A61L 2/08* (2013.01); *C12N 9/20* (2013.01); *C12N 9/94* (2013.01); *C12N 13/00* (2013.01); *C12Y 301/01003* (2013.01)

(58) Field of Classification Search
CPC ...... A61K 38/54; A61K 41/10; A61K 38/465; A61L 2/08; C12N 9/20; C12N 9/94; C12N 13/00; C12Y 301/01003
USPC ...................................................... 424/94.21
See application file for complete search history.

(56) References Cited

U.S. PATENT DOCUMENTS

| | | |
|---|---|---|
| 2,456,909 A | 12/1948 | Brasch |
| 4,623,624 A | 11/1986 | Schultze |
| 5,366,746 A | 11/1994 | Mendenhall |
| 5,782,914 A | 7/1998 | Schankereli |
| 6,203,755 B1 | 3/2001 | Odland |
| 6,685,695 B2 | 2/2004 | Ferree |
| 6,908,591 B2 | 6/2005 | MacPhee |
| 8,283,147 B2 | 10/2012 | Kurfurst |
| 9,198,871 B2 | 12/2015 | Shlieout |
| 10,184,121 B2 | 1/2019 | Ortenzi et al. |
| 2003/0049245 A1 | 3/2003 | Mann |
| 2006/0011376 A1 | 1/2006 | Van Den Berg |
| 2009/0233344 A1 | 9/2009 | Kurfurst |
| 2010/0119654 A1 | 5/2010 | Rämsch |

FOREIGN PATENT DOCUMENTS

| | | |
|---|---|---|
| EP | 0629350 A1 | 12/1994 |
| WO | 03020324 A2 | 3/2003 |
| WO | 2007014896 A1 | 2/2007 |
| WO | 2009036842 A2 | 3/2009 |
| WO | 2015019198 A2 | 2/2015 |
| WO | 2015193730 A1 | 12/2015 |
| WO | 2017172619 A1 | 10/2017 |

OTHER PUBLICATIONS

Brahmakshatriya, V., et al., "Preliminary study for evaluation of avian influenza virus inactivation in contaminated poultry products using electron beam irradiation," Avian Pathology, 2009, vol. 38(3), pp. 245-250.
De Fiebre, C. W., et al., "Elimination of Salmonellae from Animal Glandular Products," Applied Microbiology, 1969, vol. 17(3), pp. 344-346.
Ferdes O., et al., IAEA-SM-350/25 The Use of Different Type of Electron Beam Radiation Equipment for Biotechnological Materials, Jan. 1, 1998, XP055379497, [retrieved on Jun. 8, 2017], Retrieved from the Internet:, pp. 361-375.
Gestin, M., et al., "In vitro hydrolysis by pancreatic elastases I and II reduces beta-lactoglobulin antigenicity" Lait, 1997, 77, pp. 399-409.
Hoburg, A.T., et al., "Effect of Electron Beam Irradiation on Biomechanical Properties of Patellar Tendon Allografts in Anterior Cruciate Ligament Reconstruction," The American Journal of Sports Medicine, 2010, vol. 38(6), pp. 1134-1140.
International Search Report and Written Opinion for Application No. PCT/US2017/024315, dated Jun. 20, 2017, 11 pages.
(Continued)

*Primary Examiner* — Jennifer M. H. Tichy
(74) *Attorney, Agent, or Firm* — Neal, Gerber & Eisenberg LLP

(57) ABSTRACT

The present invention pertains to an enzyme preparation obtained from e-beam irradiated animal tissue, such as porcine pancreas. The present invention also pertains to methods for making such enzyme preparations, pharmaceutical compositions comprising such enzymes preparations, and methods for using such pharmaceutical compositions and enzyme preparations.

35 Claims, No Drawings

(56) References Cited

OTHER PUBLICATIONS

Pasupuleti, V.K., et al., "State of the Art Manufacturing of Protein Hydrolysates," in Protein Hydrolysates in Biotechnology, 2010, pp. 11-32.
Penn State College of Agricultural Sciences. (2000). "Questions and Answers About Irradiation of Meats," University Park, PA. 2 pages.
Pillai, S.D., "Electronic Pasteurization of Foods" IFT Distinguished Lecturer presentation at New Jersey IFT Branch Meeting Princeton, New Jersey May 2008, 60 pages.
Preuss, T., et al., "Comparison of Two Different Methods for Inactivation of Viruses in Serum," Clinical and Diagnostic Laboratory Immunology, 1997, vol. 4(5), pp. 504-508.
Quehl, A., et al., "Disinfection of pancreatin preparations with gamma rays," NAHRUNG, 1985, vol. 29(1), pp. 105-107.
Schmidt, T., et al., "Inactivation Effect of Standard and Fractionated Electron Beam Irradiation on Enveloped and Non-Enveloped Viruses in a Tendon Transplant Model," Transfus Med Hemother, 2012, vol. 39, pp. 29-35.
Scientific Protein Laboratories, Letter to FDA dated Jun. 22, 2004, 12 pages.
Gennaro A.R., ed., Remington's Pharmaceutical Sciences, 18th Edition, Mack Publishing Company, 1990, Table of Contents, 5 pages.
Gennaro A.R., ed., Remington: The Science and Practice of Pharmacy, 19th Edition, Mack Publishing, 1995, Table of Contents, 4 pages.
Goodman and Gilman's, The Pharmacological Basis of Therapeutics (Louis S. Goodman and Lee E. Limbird, editors, McGraw Hill, 1992.
Kibbe A.H., ed., Handbook of Pharmaceutical Excipients, 3rd Edition, American Pharmaceutical Association, 1999.
Pharmaceutical Codex: Principles and Practice of Pharmaceutics 12th Edition ,Walter Lund editor, Pharmaceutical Press, London, 1994.
Reed L.J., et al., "A Simple Method of Estimating Fifty Percent End Points," American Journal of Hygiene, 1938, vol. 27 (3), pp. 493-497.
The United States Pharmacopeia:The National Formulary in: Alcohol ,United States Pharmacopeial Convention Inc, 1995, pp. 42-43.
Nims, R.W., et al., "Efficacy of Electron Beam for Viral Inactivation," Journal of Microbial & Biochemical Technology, 2015, vol. 7(4), pp. 173-176.

ENZYME COMPOSITIONS WITH REDUCED VIRAL AND MICROBIAL CONTAMINATION

CROSS-REFERENCE TO RELATED APPLICATIONS

This application is a continuation-in-part of U.S. application Ser. No. 15/470,386, filed on Mar. 27, 2017, which claims priority to U.S. Provisional Application No. 62/314,048, filed Mar. 28, 2016, U.S. Provisional Application No. 62/452,746, filed Jan. 31, 2017, and U.S. Provisional Application No. 62/454,184, filed Feb. 3, 2017, the entire contents of which are incorporated herein by reference.

JOINT RESEARCH AGREEMENT

Subject matter disclosed in this application was made by or on behalf of AbbVie Inc. and/or Abbott Laboratories, whom are parties to a joint research agreement that was in effect on or before the effective filing date of this application, and such subject matter was made as a result of activities undertaken within the scope of the joint research agreement.

TECHNICAL FIELD

The present invention relates to enzyme preparations derived from animal tissue, pharmaceutical compositions comprising such enzyme preparations, and methods for reducing the risk of viral and microbial contamination in such preparations and compositions. Exemplary enzyme compositions include pancreatic extracts suitable for therapeutic use, such as for the treatment and/or prophylaxis of maldigestion, and in particular maldigestion based on chronic exocrine pancreatic insufficiency, in mammals and humans.

BACKGROUND

Products derived from animal tissue may exhibit viral and/or microbial contamination. Certain biological contaminants such as bacteria or protozoa may be inactivated during manufacturing processes. However, other biological contaminants such as non-enveloped viruses and certain spore-forming bacteria (e.g., *Bacillus cereus*) are resistant to established methods for reduction or inactivation of contaminants. A particular challenge is the inactivation or removal of viruses and spore-forming bacteria from enzyme compositions derived from animal tissue without destroying or changing the activity of the enzymes in the process.

Established methods for viral inactivation include, for example, pasteurization, dry heat, vapor heat, solvent/detergent treatment, and low pH. The selection of the methods to be employed for viral inactivation depend on the nature and contamination of the product, the method of purification used, if any, and the nature of the viral contaminant. For example, solvent or detergent treatment can disrupt the lipid membrane of enveloped viruses and has thus been used for inactivation of enveloped viruses. However, many non-enveloped viruses are generally not inactivated by solvent or detergent treatment. Similarly, many spore-forming bacteria are resistant to both heat and organic solvents.

Heat, in particular dry heat, is another established method for viral inactivation. While dry heat treatment may inactivate even highly resistant viruses, such as non-enveloped viruses, the treatment requires extended time periods (of several hours) and monitoring of moisture content. Moreover, heat treatment can compromise the desired biological activity of the product, particularly where the product is an enzyme composition.

Pancreatic enzyme products have long been used to treat exocrine pancreatic insufficiency, a condition associated with cystic fibrosis (CF), chronic pancreatitis, obstruction of the pancreas or common bile duct (such as from a neoplastic disease), surgical procedures such as pancreatectomy or gastrointestinal bypass surgery, as well as other diseases and disorders. The pancreas secretes digestive enzymes, including lipases, proteases, and amylases, into the proximal duodenal lumen, where they facilitate the hydrolysis of macronutrients. Amylases and proteases are secreted by organs other than the pancreas, and these contribute to the digestion of carbohydrates and protein. However, there is relatively little lipase from sources other than the pancreas involved in digestion of lipids. Thus, patients with untreated exocrine pancreatic insufficiency typically have difficulty digesting fat and may suffer symptoms of maldigestion or malnutrition or both, with deficiencies of essential fatty acids and fat-soluble vitamins, weight loss, cramping, flatulence, bloating, and greasy, foul-smelling, loose stools (steatorrhea). For patients with CF, inadequate treatment may have serious consequences, as good nutritional status has been directly correlated with good lung function.

Pancreatic enzyme therapy treats and/or avoids malabsorption and facilitates growth and development in patients with exocrine pancreatic insufficiency. In patients with CF, mucus blocks the pancreatic duct in the pancreas as it does in the lungs. The pancreatic digestive enzymes are not secreted into the intestine, and thereby digestion of starch, fat, and protein is impaired. The lack of digestion results in steatorrhea, abdominal pain, and weight loss, among others.

Maldigestion in mammals and humans is usually based on a deficiency of digestive enzymes, in particular on a deficiency of endogenous lipase, but also of protease and/or amylase. If the pancreatic insufficiency is pathological, this may be congenital or acquired. Acquired chronic pancreatic insufficiency may, for example, be ascribed to alcoholism. Congenital pancreatic insufficiency may, for example, be ascribed to the congenital disease cystic fibrosis. The consequences of the deficiency of digestive enzymes may be severe symptoms of under-nutrition and malnutrition, which may be accompanied by increased susceptibility to secondary illnesses.

Substitution with exogenous digestive enzymes or mixtures of digestive enzymes (i.e., pancreatic enzyme therapy) has proved an effective treatment for a deficiency in endogenous digestive enzymes. Most frequently, pharmaceutical preparations containing porcine pancreatin are used for pancreatic enzyme therapy (also known as "enzyme substitution therapy"). For such pharmaceutical preparations, the active ingredient evaluated in clinical trials is lipase and dosage amounts for commercial products are given in lipase units. Nevertheless, such mixtures of digestive enzymes obtained from the pig pancreas comprise lipases, amylases and proteases, and can be used effectively for pancreatic enzyme therapy in humans owing to the great similarity of the enzymes and accompanying substances contained therein to the contents of human pancreatic juices. The pancreatic enzymes are usually administered orally in the form of solid preparations.

Pancreas glands may be obtained from animals, such as pigs, raised and slaughtered for food. Governmental regulations often require that pancreas glands be obtained from a single species slaughterhouse (i.e., no other species are slaughtered and processed at that facility) and, thereby limit the availability of starting material. Wide-spread contamination of facilities with infectious agents may lead to a shutdown of production and to supply shortfall. Current testing procedures may identify contaminated lots and elimination of such lots place further burdens on an already constrained supply of starting material.

Processes to obtain pancreatic enzyme(s) from a mammalian pancreas gland are available. For example, processes are described in U.S. Pat. No. 4,623,624 by which pancreatin is obtained through autolysis of an aqueous isopropanol-containing tissue slurry.

The presence of infectious agents, and in particular viruses and spore-forming bacteria, in porcine pancreas used for manufacture of pancreatin is recognized. Indeed, most swine herds have been infected with porcine parvovirus (PPV), which has a high resistance to inactivation. PPV has been detected in pancreatin as an infectious agent. Although, PPV is not believed to be pathogenic for humans, it is desirable to obtain pancreatin with a reduced PPV load. In addition, PPV is a common model virus as it is difficult to inactivate by standard methods, such as chemical or thermal processing. Likewise, contamination of pancreatin drug substance with *Bacillus cereus* and/or *Bacillus cereus* enterotoxin has been reported.

US 2010/0119654 relates to irradiation of an alcoholic or aqueous biological extract which contains solids in the form of a suspension. The radiation employed in US 2010/0119654 is ultra-violet (UV) radiation, x-ray radiation, 0 radiation, or γ-radiation. UV irradiation of a pancreatin intermediate dissolved in 40% isopropanol produced up to 4 $\log_{10}$ reduction in M2 phage. Gamma-irradiation of pancreatin (API) produced an approx. 40% decrease in lipase activity at 27 kGy and a 13% decrease in lipase activity at 5 kGy. Bacterial content was reduced by more than 2.5 $\log_{10}$ but virus inactivation was not reported. When pancreatin (API) was treated with β-irradiation, >85% enzyme activity was reportedly maintained, but "germ count" was only reduced by approx. 1.5 $\log_{10}$.

WO 2003/020324 relates to sterilizing digestive enzymes, such as trypsin, α-galactosidase, and iduronate 2-sulfatase, with irradiation. Lyophilized or liquid enzymes (trypsin, a glycosidase, or a sulfatase) were irradiated alone or in the presence of a stabilizer. γ-irradiation was accomplished using a $^{60}$Co source. Viral inactivation was not reported.

WO 2007/014896 relates to reducing the concentration of one or more biological, in particular viral, contaminants of pancreatin by heating the pancreatin.

In US 2009/0233344, heat treatment of pancreatin at 80° C. for 32 hours provided about 2.5 $\log_{10}$ reduction in PPV viral titer but also a 20% loss in lipase activity. Heat treatment of pancreatin at 100° C. for 8 hours provided a greater than 3 $\log_{10}$ reduction in PPV viral titer, but nearly 50% of lipase activity was lost.

Thus, process steps that can be effective against difficult-to-inactivate viruses, such as PPV, have a high potential for changing the nature of the pancreatin product by degrading or reducing the pancreatic enzymes, particularly lipase, to unacceptable levels. Such changes in potency may reduce or alter the efficacy profile of the ultimate product. Therefore, it is desirable to maintain enzyme activity, particularly lipase activity, during the manufacturing process.

Since each of the previously tested viral clearance processes that demonstrated some effectiveness against difficult-to-inactivate viruses (e.g., PPV) resulted in significant loss of enzyme activity, including lipase activity, there was skepticism in the industry that a robust level of viral inactivation/clearance could be achieved without compromising product quality. In particular, there was skepticism in the industry that a suitable robust, orthogonal viral clearance step could be developed without adversely impacting the chemical, physical, or pharmaceutical properties of pancreatin. See, e.g., Letter from Scientific Protein Laboratories to FDA dated Jun. 22, 2004 in Docket No. 2003D-0206.

SUMMARY OF THE INVENTION

The present invention pertains to an enzyme preparation isolated from an animal tissue source. The isolated enzyme preparation includes one or more enzymes, has a reduced viral and/or microbial contamination relative to the source animal tissue, and maintains at least one biological activity of the source animal tissue. In certain embodiments, the enzyme preparation is produced by subjecting the source animal tissue to radiation, preferably electron beam radiation, and subsequently isolating one or more enzymes from the irradiated tissue. In certain embodiments, the source animal tissue is intact tissue. In certain embodiments, the irradiated tissue exhibits at least a three $\log_{10}$, preferably at least a four $\log_{10}$, reduction in viral and/or microbial contaminants compared to non-irradiated source animal tissue. In certain embodiments, the irradiated tissue exhibits at least a three $\log_{10}$, preferably at least a four $\log_{10}$, reduction in viral load compared to the source animal tissue. In certain embodiments, additional, orthogonal viral reduction steps are employed (e.g., during the step of isolating one or more enzymes from the irradiated tissue). In certain embodiments, the enzyme preparation isolated from the irradiated tissue has a biological activity corresponding to at least 50%, preferably at least 90%, of the biological activity of a control enzyme preparation, such as an enzyme preparation isolated from non-irradiated source animal tissue. In certain embodiments, the biological activity is lipase activity. In certain embodiments, the irradiated tissue exhibits at least a three $\log_{10}$, preferably at least a four $\log_{10}$, reduction in viral and/or microbial contaminants compared to non-irradiated source animal tissue and the enzyme preparation isolated from the irradiated tissue has a biological activity corresponding to at least 50%, preferably at least 90%, of the biological activity of a control enzyme preparation, such as an enzyme preparation isolated from non-irradiated source animal tissue.

Another aspect of the present invention pertains to a method for producing an enzyme preparation derived from an animal tissue, wherein the enzyme preparation has a reduced viral and/or microbial contamination relative to the source animal tissue. The method includes a treatment sufficient to produce at least a three $\log_{10}$, preferably at least a four $\log_{10}$, reduction in viral and/or microbial contaminants compared to the source animal tissue. In certain embodiments, the treatment comprises subjecting intact source animal tissue to radiation, preferably electron beam radiation, to produce irradiated animal tissue. In certain embodiments, the electron beam radiation treatment is sufficient to reduce viral and/or microbial contamination of the source animal tissue, while maintaining at least one biological activity of the source animal tissue. In certain embodiments, the biological activity is lipase activity. In certain embodiments, one or more enzymes and/or proenzymes are extracted from the irradiated animal tissue. In certain embodiments, one or more enzymes are isolated from the irradiated animal tissue. In certain embodiments, the method reduces the risk of infectious contamination of the animal-derived enzyme preparation or a pharmaceutical composition comprising the animal-derived enzyme preparation relative to an untreated control.

Another aspect of the present invention pertains to a pharmaceutical composition comprising the enzyme preparations described herein. The pharmaceutical composition may be an oral pharmaceutical dosage form. In certain embodiments, the pharmaceutical composition is used to treat or prevent a disease responsive to pancreatic enzyme replacement therapy, such as exocrine pancreatic insufficiency. Thus, another aspect of the present invention pertains to a method for treating or preventing exocrine pancreatic insufficiency comprising administering to a subject in need thereof a dose of an enzyme preparation or pharmaceutical composition described herein.

Another aspect of the present invention pertains to kits that comprise the enzyme preparations or pharmaceutical compositions described herein.

These and other objects of the invention are described in the following paragraphs. These objects should not be deemed to narrow the scope of the invention.

DETAILED DESCRIPTION OF THE INVENTION

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. DEFINITIONS

As used in the specification and the appended claims, unless specified to the contrary, the following terms have the meaning indicated:

The term "API" as used herein stands for "active pharmaceutical ingredient." The preferred API as disclosed herein is pancreatin, in particular porcine pancreatin as generally used for therapeutic purposes, i.e., pancreatin according to the requirements of standard pharmacopoeias, e.g. Ph. Eur. and/or USP and suitable for oral administration in the treatment or prophylaxis of maldigestion in mammals, in particular humans, and in particular of maldigestion due to chronic exocrine pancreatic insufficiency such as in patients suffering from cystic fibrosis, chronic pancreatitis or patients who have undergone upper gastrointestinal surgery.

The term "crude" as used herein refers to a non-purified preparation or mixture containing enzymes and/or proenzymes as well as additional components derived from the source tissue. A crude preparation or mixture includes, but is not limited to, animal tissue itself.

The term "enzyme preparation" refers to any composition of matter containing one or more enzymes, whether in the active or inactive form (i.e., proenzymes or zymogens). The term includes cell or tissue extracts as well as crude preparations derived from animal tissue or other cellular material. One example of an enzyme preparation is pancreatin, pancrelipase, an extract derived from mammalian, preferably porcine, pancreatic glands.

The term "extract" as it relates to the present enzyme preparations refers to one or more enzymes and/or proenzymes that have been separated from at least one component of the tissue from which they were derived. Extracted components may be in the form of an active enzyme or a proenzyme (zymogen) requiring subsequent conversion to the active form.

The term "isolate" as it relates to the present enzyme preparations refers to one or more active enzymes that have been separated from at least one component of the tissue from which they were derived. Thus, in certain embodiments, an "isolated enzyme" or an "isolated enzyme preparation" includes one or more active enzymes that have been converted from the corresponding proenzyme form via hydrolysis and/or autolysis. Hydrolysis and/or autolysis to convert the proenzyme to an active enzyme may occur before, during, or after extraction.

The terms "pancreatic enzymes", "pancreatin" and "pancrelipase" as used herein refer to enzymatic mixtures derived from mammalian pancreatic glands comprising digestive enzymes such as lipase, protease and amylase as main components. In particular, the terms "pancreatic enzymes", "pancreatin" and "pancrelipase" may be used synonymously herein and refer to pancreatic extracts suitable for therapeutic use, in accordance with standard pharmacopoeias, which contain several digestive enzymes whose properties are defined by standard monographs as explained above. Due to standard manufacturing processes, "pancreatic enzymes", "pancreatin" and "pancrelipase" are usually provided in powder form as "pancreatin powder", sometimes also referred to as "pancreas powder". Pancreatic enzymes, pancreatin and pancrelipase also can be, and preferably are, APIs. Pancreatin for pharmaceutical use is typically of bovine or porcine origin. Porcine pancreatin is preferred. Pancrelipase has been described in some references as an enzyme preparation with increased activity (lipase) relative to pancreatin.

As used herein, the term "pharmaceutical composition" means a composition comprising an enzyme preparation as described herein and optionally one or more pharmaceutically acceptable excipients.

The term "pharmaceutically acceptable" is used adjectivally to mean that the modified noun is appropriate for use as a pharmaceutical product or as a part of a pharmaceutical product.

An "orthogonal" microbial and/or viral reduction step refers to a distinct method for reduction of the microbes and/or viruses that may be present in a sample. A microbial and/or viral reduction step can be orthogonal provided that there are one or more additional microbial and/or viral reduction steps in the process. In certain embodiments, an "orthogonal" microbial and/or viral reduction step has a sufficiently distinct mechanism from all other microbial and/or viral reduction steps used in the process such that the $\log_{10}$ kill achieved by the "orthogonal" step becomes additive with the cumulative $\log_{10}$ kill achieved from the all other microbial and/or viral reduction steps that are used for obtaining the enzyme preparation.

The terms "prevent", "preventing" and "prevention" refer to a method of preventing the onset of a condition, disorder, or disease and/or the attendant symptoms thereof or barring a subject from acquiring a condition, disorder, or disease. As used herein, "prevent", "preventing" and "prevention" also include delaying the onset of a condition, disorder, or disease and/or the attendant symptoms thereof and reducing a subject's risk of acquiring a condition, disorder, or disease.

The term "subject" includes humans and other primates as well as domesticated and semi-domesticated animals including, but not limited to, poultry, honeybees, cows, sheep, goats, pigs, horses, dogs, cats, rabbits, rats, mice and the like. The term "poultry" encompasses all types of domestic fowl, including, but not limited to chickens, turkey, ducks, geese, the ratite group of birds and game birds. In certain embodiments, the subject is a human The term "therapeutically effective amount" means a sufficient amount of the enzyme preparation or pharmaceutical composition to treat a condition, disorder, or disease, at a reasonable benefit/risk ratio applicable to any medical treatment. When used in a medical treatment, a therapeutically effective amount of one of the enzyme preparations can be employed as an extract or in a crude form. Alternatively, the enzyme composition can be administered as a pharmaceutical composition containing the enzyme composition of interest in combination with one or more pharmaceutically acceptable carriers.

The terms "treat", "treating" and "treatment" refer to a method of alleviating or abrogating a condition, disorder, or disease and/or the attendant symptoms thereof.

B. ENZYME PREPARATIONS AND METHODS OF MANUFACTURE

In one aspect, the present invention includes an enzyme preparation comprising one or more enzymes and/or proenzymes derived from animal, preferably mammalian, tissue. In certain embodiments, the enzyme preparation comprises a mixture of digestive enzymes and/or proenzymes. In certain embodiments, the enzyme preparation comprises a lipase. In certain embodiments, the enzyme preparation comprises an amylase. In certain embodiments, the enzyme preparation comprises a protease. In certain embodiments, the enzyme preparation comprises pancreatin. In certain embodiments, the enzyme preparation comprises a proenzyme, such as a prolipase or a typsinogen. In certain embodiments, the enzyme preparation is in a crude form. In certain embodiments, the enzyme preparation comprises one or more enzymes and/or proenzymes that have been extracted from an animal tissue. In certain embodiments, the enzyme preparation comprises one or more enzymes that have been isolated from an animal tissue.

In certain aspects, an isolated enzyme preparation has the same or substantially the same biological activity, but less infectiousness, as the tissue from which it was isolated. In certain embodiments, the isolated enzyme preparation has the same or substantially the same biological activity as a control enzyme preparation. In certain embodiments, the infectiousness of the isolated enzyme preparation is reduced by at least three $\log_{10}$, preferably at least four $\log_{10}$, relative to the infectiousness of the tissue from which it was isolated. In certain embodiments, the infectiousness that is reduced is viral infectiousness, particularly, non-enveloped viral infectiousness and/or enveloped virus infectiousness. In certain embodiments, a biological activity of the isolated enzyme preparation is at least 50%, at least 60%, at least 70%, at least 80%, or preferably at least 90%, of the biological activity of a control enzyme preparation. In certain embodiments, the biological activity is enzymatic activity, such as protease activity, amylase activity, or, preferably, lipase activity.

In another aspect, the enzyme preparation is isolated from a pre-treated tissue source and has the same or substantially the same biological activity, but less infectiousness, than a control preparation isolated from an untreated tissue source. In certain embodiments, the infectiousness of the enzyme preparation is reduced by at least a three $\log_{10}$, preferably at least a four $\log_{10}$, relative to the control preparation. In certain embodiments, the infectiousness of the pre-treated tissue source is reduced by at least a three $\log_{10}$, preferably at least a four logo, relative to the untreated tissue source. In certain embodiments, the infectiousness that is reduced is viral infectiousness, particularly, non-enveloped viral infectiousness. In certain embodiments, a biological activity of the enzyme preparation is at least 50%, at least 60%, at least 70%, at least 80%, or preferably at least 90%, of the biological activity of a control preparation isolated from an untreated tissue source. In certain embodiments, the biological activity is enzymatic activity, such as protease activity, amylase activity, or, preferably, lipase activity.

In another aspect, the enzyme preparation is derived from an electron beam irradiated tissue. In certain embodiments, the electron beam irradiated tissue is a mammalian, preferably porcine, tissue. In certain embodiments, the enzyme preparation derived from electron beam irradiated tissue comprises pancreatin. In certain embodiments, the enzyme preparation derived from electron beam irradiated tissue comprises a proenzyme, such as a prolipase or a typsinogen. In certain embodiments, the enzyme preparation derived from electron beam irradiated tissue is in a crude form. In certain embodiments, the enzyme preparation derived from electron beam irradiated tissue comprises one or more enzymes and/or proenzymes that have been extracted from the irradiated tissue. In certain embodiments, the enzyme preparation derived from electron beam irradiated tissue comprises one or more enzymes that have been isolated from the irradiated tissue.

In another aspect, the enzyme preparation is isolated from an electron beam irradiated tissue and has the same or substantially the same biological activity, but less infectiousness, than a control preparation isolated from a non-irradiated tissue source. In certain embodiments, the irradiated tissue is pancreatic tissue. In certain embodiments, the irradiated tissue is flaked pancreatic tissue, a whole pancreas gland, or a portion of a whole pancreas gland. In certain embodiments, the non-irradiated tissue source is pancreatic tissue. In certain embodiments, the infectiousness of the enzyme preparation is reduced by at least a three $\log_{10}$, preferably at least a four $\log_{10}$, relative to the control preparation. In certain embodiments, the infectiousness that is reduced is viral infectiousness, particularly, non-enveloped and/or enveloped viral infectiousness. In certain embodiments, the infectiousness that is reduced is PPV infectiousness. In certain embodiments, a biological activity of the isolated enzyme preparation is at least 50%, at least 60%, at least 70%, at least 80%, or preferably at least 90%, of the biological activity of the control preparation. In certain embodiments, the biological activity is enzymatic activity, such as protease activity, amylase activity, or, preferably, lipase activity.

In another aspect, the enzyme preparation comprises electron beam irradiated proenzymes. In certain embodiments, the enzyme preparation is further processed, such as by converting the irradiated proenzymes into their active form (e.g., by autolysis and/or hydrolysis).

The present enzyme preparations can be better understood in connection with the following methods which illustrate exemplary techniques by which the enzyme preparations can be obtained.

In one aspect, the present invention includes a method for manufacturing an enzyme composition comprising subjecting a proenzyme source to radiation, preferably electron beam radiation. In certain embodiments, the proenzyme source is a population of cells. In certain embodiments, the population of cells is intact tissue obtained from a mammalian gland or a portion thereof. In certain embodiments, the population of cells is a whole gland obtained from a mammal. In certain embodiments, the population of cells is a portion of a gland obtained from a mammal. In certain embodiments, the population of cells is a frozen tissue block. In certain embodiments, the population of cells is flaked or minced animal tissue.

In another aspect, the present invention includes a method for manufacturing an enzyme preparation. The method comprises subjecting an animal tissue to radiation, preferably electron beam radiation. In certain embodiments, the animal tissue is an intact tissue. In certain embodiments, the intact animal tissue is a frozen tissue block. In certain embodiments, the intact animal tissue is flaked or minced animal tissue.

In certain embodiments, the method begins with animal tissue, preferably intact animal tissue. In certain embodiments, the animal tissue is mammalian, and preferably porcine, pancreas. In certain embodiments, porcine pancreas is procured from an approved slaughterhouse, preferably a single species slaughterhouse.

In certain embodiments, intact animal tissue includes intact pancreatic tissue. In certain embodiments, intact pancreatic tissue includes a whole pancreas gland or a portion thereof, such as one or more lobes. In certain embodiments, intact pancreatic tissue includes flaked frozen tissue. In certain embodiments, intact pancreatic tissue includes a frozen tissue block, which may have been mechanically processed. In certain embodiments, intact pancreatic tissue includes pancreatic tissue that has been minimally manipulated or altered, or preferably not manipulated or altered, in such a way as to, for example, destroy active enzymes and/or convert proenzymes in the tissue to their active form. For example, a tissue homogenate that undergone significant chemical or enzymatic processing to convert proenzymes to their active form is not "intact tissue" as the term is used herein. As another example, tissue that has been ground or minced under conditions that destroy active enzymes and/or convert proenzymes in the tissue to their active form is not "intact tissue" as the term is used herein.

Mincing typically involves processing the source tissue in a grinder into pieces no greater than 0.5 cm$^3$, no greater than 0.4 cm$^3$, no greater than 0.3 cm$^3$, no greater than 0.2 cm$^3$, or no greater than 0.1 cm$^3$. Homogenization typically involves mixing minced material with water to form a slurry or suspension as known in the art. The tissue may also be mixed with other solutions and/or stabilizers to enable or ease mechanical processing, provided that the mixing with other solutions and/or stabilizers does not destroy active enzymes and/or convert proenzymes in the tissue to their active form, e.g., by maintaining the temperature of the homogenate, suspension or slurry at 10° C.+5° C., preferably, below 10° C.

Thus, mechanical processing of tissue explicitly encompasses the addition of or mixing with water and/or a lower alcohol (e.g., isopropyl alcohol) in sufficient amount to enable or ease mechanical processing such as mincing or homogenization, provided that the mixing/combination is not accompanied by concomitant autolysis or hydrolysis. Thus, mechanical processing according to the methods of the invention can be performed to maintain the tissue at 10° C.+5° C., preferably below 10° C. (including freezing), during processing to minimize or halt the autolysis or hydrolysis. Accordingly, for example, a tissue homogenate may be a mixture of both tissue and water, which has been maintained at 10° C.+5° C., preferably below 10° C., during processing so as to prevent the tissue from undergoing hydrolysis and/or autolysis.

In contrast, "in-process intermediate" (and analogous terms) references tissue that, in addition to optional mechanical alteration from source tissue, has also been subject to one or more steps of chemical and/or enzymatic processing, including hydrolysis and autolysis. In particular, the one or more steps of chemical and/or enzymatic processing alter the biomolecule population and/or biomolecule profile by, for example, destroying active enzymes and/or converting proenzymes in the tissue to their active form. Thus, an in-process intermediate may also have an altered ratio of pro-enzyme(s) to active enzyme(s).

In certain embodiments, the animal tissue, preferably frozen animal tissue, is comminuted. In certain embodiments, comminution can be achieved using a frozen block flaker, such as a Hydrauflake Chunker provided by General Machinery Corporation (Sheboygan, Wis.), which is designed to chunk frozen tissue in preparation for further processing.

In certain embodiments, the animal tissue is irradiated. In certain embodiments, the animal tissue is exposed to a sterilizing beam of accelerated electrons, i.e., an E-beam or electron beam radiation. In certain embodiments, intact animal tissue is exposed to electron beam irradiation. In certain embodiments, a whole pancreas gland or an intact portion thereof is exposed to electron beam irradiation. In certain embodiments, flaked porcine pancreatic tissue is exposed to electron beam irradiation.

E-beam radiation is a form of ionizing energy that is generally characterized by its low penetration and high dosage rates. The beam, a concentrated, highly charged stream of electrons, is generated by the acceleration and conversion of electricity. The electrons are generated by equipment referred to as accelerators, which are capable of producing beams that are either pulsed or continuous. As the material being irradiated passes beneath or in front of the electron beam, energy from the electrons is absorbed. This absorption of energy alters various chemical bonds and biological properties within the product/material. The energy that is absorbed is referred to as the "absorbed dose." It is this absorption of energy—or "dose delivery"—that destroys viruses and microorganisms, e.g., by destroying their DNA or RNA chains.

Irradiation may be carried out in a conventional manner, such as by placing the tissue in a suitable container and exposing the tissue to an electron beam. In certain embodiments, the container holding the tissue is placed on a conveyor which then passes through the electron beam. In certain embodiments, the container holding the tissue does not contain any solvent. In certain embodiments, the container holding the tissue is substantially free of solvent. In certain embodiments, the container holding the tissue does not contain any flammable solvent. In certain embodiments, the container holding the tissue is substantially free of a flammable solvent, such as alcohol. For example, the container may contain frozen, intact tissue such as a whole gland, a portion of a whole gland, or flaked tissue.

In certain embodiments, the radiation is provided at a dose sufficient to substantially inactivate resistant viruses and/or microbes in the tissue. In certain embodiments, the radiation is at a dose that prevents loss of a biological activity, preferably an enzymatic activity, relative to a control enzyme preparation isolated from non-irradiated tissue.

The beam of accelerated electrons may be provided by an electron accelerator, such as an electron accelerator provided by Iotron Industries USA, Inc. (Columbia City, Ind.). In certain embodiments, the electron accelerator operates at powers from 20 to 250 kW and beam energies from 5 to 18 mega electron-volts (MeV). In certain embodiments, the electron accelerator operates at 60 kW and 10 MeV. In certain embodiments, the electron accelerator provides a beam energy of 10 MeV or above.

A tissue can be exposed to electron beam irradiation for a time and in an amount sufficient to achieve viral or microbial inactivation without compromising a biological activity of one or more enzymes subsequently extracted or isolated from the irradiated tissue. The dosage of electron beam irradiation required to sterilize a tissue can vary based on, for example, the size of the tissue, the type of the tissue, and the type and amount of viral or microbial contaminant in, or suspected of being present in, the tissue sample. One skilled in the art will recognize and be able to determine an appropriate dose and time suitable for a particular tissue and based on the characteristics of the tissue and accelerator being used. The electron beam dose selected is effective for inactivation of infectious agents that are difficult to destroy by conventional processes while causing minimal loss in enzyme activity.

An "absorbed dose" of radiation is expressed in terms of kilograys (kGy), wherein one kilogray is equal to one thousand joules of energy deposited per kilogram of material. In certain embodiments, the tissue is exposed to the electron beam until an infectious agent-inactivating amount of radiation is absorbed. For example, the tissue may be exposed to the electron beam until a dose of about 10, about 15, about 20, about 25, about 30, about 35, about 40, about 45, or about 50 kilograys (kGy) or more is achieved. As another example, the tissue may be exposed to the electron beam until a dose of about 5 to about 50, about 10 to about 40, about 15 to about 35 kGy is achieved. In certain embodiments, the tissue is exposed to the electron beam until a dose of about 30 kGy is absorbed. In certain embodiments, porcine pancreas is irradiated with an electron beam dose sufficient to provide a high $\log_{10}$ kill for infectious agents, preferably infectious agents that are difficult to inactivate such as non-enveloped viruses, while causing minimal loss in enzyme activity.

In certain embodiments, dosage can be determined with the use of radiochromic dye films. Such films can be calibrated by reference to a national standard.

In certain embodiments, the tissue is exposed to electron beam radiation for a time and in an amount sufficient to produce at least a three $\log_{10}$, preferably at least a four $\log_{10}$, reduction in viral load of a model virus compared to a control sample. In some such embodiments, the tissue is exposed to electron beam radiation for a time and in an amount sufficient to produce between about three $\log_{10}$ and about five $\log_{10}$ reduction in viral load of a model virus compared to a control sample. In some such embodiments, the tissue is exposed to electron beam radiation for a time and in an amount sufficient to produce about four $\log_{10}$ reduction in viral load of a model virus compared to a control sample. In certain embodiments, the model virus is PPV. In certain embodiments, the tissue is intact tissue. In some such embodiments, the intact tissue is a gland, such as a whole pancreas gland or a portion thereof, such as one or more lobes of a pancreas gland. In other such embodiments, the intact tissue is frozen, flaked tissue.

In certain embodiments, the electron beam exposure includes single-sided or multiple-sided exposure. In certain embodiments, the tissue is subjected to a one-sided exposure to the electron beam. In certain embodiments, the tissue is subjected to a multiple-sided exposure, for example, a two-sided exposure to the electron beam. Thus, a dose of about 20 kGy may comprise a two-sided exposure at about 10 kGy/side; a dose of about 30 kGy may comprise a two-sided exposure at about 15 kGy/side; a dose of about 40 kGy may comprise a two-sided exposure at about 20 kGy/side; and a dose of about 50 kGy may comprise a two-sided exposure at about 25 kGy/side.

In certain embodiments, the methods of manufacturing the enzyme preparation reduce the risk of viral or microbial infectiousness of a pharmaceutical composition comprising the enzyme preparation.

In certain embodiments, infectiousness of an irradiated pancreas gland is reduced by at least a three $\log_{10}$, preferably at least a four $\log_{10}$, relative to the infectiousness of the gland prior to radiation treatment. In certain embodiments, infectiousness of an enzyme preparation derived or isolated from an irradiated pancreas gland is reduced by at least a three $\log_{10}$, preferably at least a four $\log_{10}$, relative to the infectiousness of the gland prior to radiation treatment. Alternatively, the infectiousness of the enzyme preparation is determined relative to a control enzyme preparation derived or isolated from a non-irradiated pancreas gland.

In certain embodiments, the infectiousness that is reduced is viral infectiousness, particularly, the viral infectiousness of a non-enveloped virus such as PPV. For example, PPV infectiousness of a pancreatin product isolated from an irradiated pancreas gland is reduced by at least a three $\log_{10}$, preferably at least a four $\log_{10}$ relative to a control enzyme preparation isolated from a non-irradiated pancreas gland. As another example, PPV infectiousness of an irradiated pancreas gland is reduced by at least a three $\log_{10}$, preferably at least a four $\log_{10}$ relative to a non-irradiated pancreas gland. In some such embodiments, the PPV infectiousness of an enzyme preparation is further reduced by subsequent, orthogonal viral inactivation steps performed following irradiation.

In certain embodiments, the methods can also include the step of, following the irradiation step, testing for the presence or amount of one or more microorganisms (e.g., viruses, bacteria, or protozoa) in the tissue or enzyme preparation derived from the tissue. Methods for determining whether a sample contains a microorganism are known in the art and include, for example, plaque-assays or colony formation tests. Effective sterilization can also be determined using conventional microbiological techniques, such as, for example, the inclusion of suitable biological indicators in a radiation batch or contacting the tissue with a culture medium, and incubating the medium to determine sterility of the tissue.

In certain embodiments, viral infectiousness can be calculated by endpoint titration and subsequent calculation of the half tissue culture infectious dose ($TCID_{50}$). The virus titres calculated in this manner can be given as $\log_{10} TCID_{50}$ per ml with confidence intervals of 95%.

In certain embodiments, a reduction in viral contamination is given in accordance with USP-NF general chapter <1050>, as a logarithmic reduction factor which is the difference in virus titre between a control sample and the sample derived from an e-beam irradiated tissue upon isolation. For example, a 3 $\log_{10}$ reduction may indicate a reduction in viral load by a factor of 1,000 and a 4 $\log_{10}$ reduction may indicate a reduction in viral load by a factor of 10,000.

In certain embodiments, the methods of manufacturing the enzyme preparation allow for the reduction of viral and/or microbial contamination of the enzyme preparation without a substantial reduction in its enzymatic activity.

In certain embodiments, enzymatic activity of an enzyme preparation isolated from an irradiated pancreas gland is maintained. For example, in certain embodiments, a biological activity of the enzyme preparation is at least 50%, at least 60%, at least 70%, at least 80%, or preferably at least 90%, of the biological activity of a control preparation isolated from a non-irradiated pancreas gland. In certain embodiments, the biological activity is enzymatic activity, such as protease activity, amylase activity, or, preferably, lipase activity.

Following irradiation, the tissue may be further processed to provide the enzyme composition. For example, in certain embodiments, one or more enzymes and/or proenzymes are extracted from the irradiated tissue. In certain embodiments, one or more enzymes are isolated from the irradiated tissue. Various methods for isolating enzymes from tissue samples are known. For example, U.S. Pat. No. 4,623,624 provides methods for isolating pancreatin by autolysis of an aqueous isopropanol-containing tissue slurry.

In certain embodiments, the irradiated tissue may be subjected to autolysis and/or hydrolysis to convert proenzymes to their active form. For example, the irradiated tissue may be combined with a hydrolysis starter to initiate autolysis. In certain embodiments, the autolysis and/or hydrolysis is carried out at ambient temperature. In certain embodiments, the reaction mixture is filtered upon completion of the reaction; the filtrate is collected; the enzymes present in the filtrate are precipitated (e.g., with isopropanol); and the precipitate is filtered, washed with isopropanol, and vacuum dried.

It can be appreciated that the methods described above and as illustrated in the Examples section are illustrative and are not to be read as limiting the scope of the invention as it is defined in the appended claims. All alternatives, modifications, and equivalents of the methods and specific examples are included within the scope of the claims.

C. COMPOSITIONS

In at least one aspect, the present invention includes compositions comprising an enzyme preparation as described herein. In certain embodiments, the composition comprises one or more enzymes and/or proenzymes extracted from an irradiated animal tissue. In certain embodiments, the composition comprises one or more enzymes isolated from an irradiated animal tissue. In certain embodiments, the composition is a crude mixture containing one or more enzymes derived from animal tissue.

In a further aspect, a pharmaceutical composition comprising an enzyme preparation as described herein is provided, further optionally comprising one or more conventional pharmaceutically acceptable excipients such as those found in textbooks such as Remington's Pharmaceutical Sciences, 18th Ed. (Alfonso R. Gennaro, ed.; Mack Publishing Company, Easton, Pa., 1990); Remington: the Science and Practice of Pharmacy 19th Ed. (Lippincott, Williams & Wilkins, 1995); Handbook of Pharmaceutical Excipients, 3rd Ed. (Arthur H. Kibbe, ed.; Amer. Pharmaceutical Assoc, 1999); the Pharmaceutical Codex: Principles and Practice of Pharmaceutics 12th Ed. (Walter Lund ed.; Pharmaceutical Press, London, 1994); The United States Pharmacopeia: The National Formulary (United States Pharmacopeial Convention); and Goodman and Gilman's: the Pharmacological Basis of Therapeutics (Louis S. Goodman and Lee E. Limbird, eds.; McGraw Hill, 1992), the disclosures of which are hereby incorporated by reference.

Pharmaceutical compositions comprising an enzyme preparation as described herein may be used to supplement digestive enzymes in the treatment and/or the prophylaxis of maldigestion in mammals, in particular of maldigestion due to chronic exocrine pancreatic insufficiency such as in patients suffering from cystic fibrosis, chronic pancreatitis or patients who have undergone upper gastrointestinal surgery. Pharmaceutical compositions or dosage forms as described herein may preferably be oral dosage forms which can in particular be administered to humans.

An oral dosage form containing an enzyme preparation may be in the form of, for example, capsules, granules, granulates, micropellets, microspheres, microtablets, pellets, pills, powders and/or tablets. For the purposes of this description, the prefix "micro" is used to describe an oral dosage form if the diameter of the oral dosage form or all of its dimensions (length, height, width) is equal to or below about 5 mm.

In certain embodiments, the oral dosage form is a capsule. The capsule may comprise between about 2,000 and about 40,000 lipase units per capsule. In certain embodiments, the oral dosage form is a capsule comprising 3,000, 6,000, 12,000, 24,000, or 36,000 lipase units per capsule. In certain embodiments, the oral dosage form is a capsule comprising 3,000, 5,000, 10,000, 15,000, 20,000, 25,000, or 40,000 lipase units per capsule. In certain embodiments, the oral dosage form is a capsule comprising 2,600, 4,200, 10,500, 16,800, or 21,000 lipase units per capsule. In certain embodiments, the oral dosage form is a capsule comprising 4,000, 13,800, 20,700, or 23,000 lipase units per capsule. In certain embodiments, the oral dosage form is a capsule comprising 4,000, 8,000, or 16,000 lipase units per capsule. In certain embodiments, the oral dosage form is a capsule comprising 4,000, 8,000, or 16,000 lipase units per capsule. In other embodiments, the oral dosage form is a capsule comprising 3,000, 4,000, 6,000, or 8,000 lipase units per capsule. Dosage strength may be expressed in a variety of ways, including in USP units, Ph. Eur. units, or BP units.

In certain embodiments, the oral dosage form is a tablet comprising 10,440 or 20,880 lipase units per tablet.

Various pharmaceutical compositions and dosage forms containing pancreatin are known, such as delayed release and immediate release compositions. For example, U.S. Pat. No. 9,198,871 provides delayed release pancreatin compositions.

In certain embodiments, the oral dosage form is a pancreatin micropellet or pancreatin microsphere. In certain embodiments, the pancreatin micropellet or pancreatin microsphere is coated with, for example, an enteric coating. In certain embodiments, the pancreatin micropellet or pancreatin microsphere—independent of any such coating—comprises between about 10% and about 95% by weight of pancreatin, between about 5% and about 90% by weight of at least one pharmaceutically acceptable binding agent, and between 0% and about 10% by weight of at least one pharmaceutically acceptable excipient. More specifically, the pancreatin micropellet or pancreatin microsphere comprises between about 70% and about 90% by weight of pancreatin, between about 10% and about 30% by weight of at least one pharmaceutically acceptable binding agent, and between 0% and about 5% by weight of at least one pharmaceutically acceptable excipient. In certain embodiments, the pancreatin micropellet or pancreatin microsphere comprises between about 70% and about 90% by weight pancreatin and between about 10% and about 30% by weight of at least one pharmaceutically acceptable binding agent. In certain embodiments, the pancreatin micropellet or pancreatin microsphere is approximately spherical and has a diameter between about 0.5 mm and about 2.0 mm. In certain embodiments, the pancreatin micropellet or pancreatin microsphere has a first dimension between about 0.5 mm and about 2.0 mm and a second dimension between about 0.5 mm and about 2.0 mm. In certain embodiments, the pancreatin micropellet or pancreatin microsphere has a first dimension between about 0.8 mm and about 1.0 mm and a second dimension between about 0.5 mm and about 2.0 mm.

Examples of pharmaceutically acceptable binding agents include polyethylene glycol 1500, polyethylene glycol 2000, polyethylene glycol 3000, polyethylene glycol 4000, polyethylene glycol 6000, polyethylene glycol 8000, polyethylene glycol 10000, hydroxypropyl methylcellulose, polyoxyethylene, copolymers of polyoxyethylen-polyoxypropylen and mixtures of said organic polymers. The foregoing list of pharmaceutically acceptable binding agents is not meant to be exhaustive, but merely illustrative as a person of ordinary skill in the art would understand that many other pharmaceutically acceptable binding agents or combination of binding agents could also be used. Polyethylene glycol 4000 is a preferred pharmaceutically acceptable binding agent.

Examples of suitable pharmaceutically acceptable excipients include gliding agents like magnesium stearate or calcium stearate, stearic acid, talcum and/or starch; fillers like calcium phosphate, corn starch, dextrans, dextrin, hydrated silicon dioxide, microcrystalline cellulose, kaolin, lactose, mannitol, polyvinyl pyrrolidone, precipitated calcium carbonate, sorbitol and/or talcum; disintegrating agents like Aerosil (silicic acid), alginic acid, amylose, calcium alginate, calcium carbonate, formaldehyde gelatin, pectic carbonate, sago starch, sodium bicarbonate and/or starch; and/or moisturizers like glycerol and/or starch. The foregoing list of pharmaceutically acceptable excipients is not meant to be exhaustive, but merely illustrative as a person or ordinary skill in the art would understand that many other pharmaceutically acceptable excipients or combination of excipients could also be used. For the purposes of the present disclosure, synthetic oils and monomeric phthalic acid esters are not to be regarded as suitable pharmaceutically acceptable excipients. In certain embodiments, the pancreatin micropellets or pancreatin microspheres contain no pharmaceutically acceptable excipients, but can optionally contain a greater amount of pancreatin.

In another embodiment, an oral dosage form, such as an enteric coated oral dosage form, of pancreatin is provided for the manufacture of a medicament for the treatment of medical conditions such as digestive disorders, pancreatic exocrine insufficiency, pancreatitis, cystic fibrosis, diabetes type I and/or diabetes type II.

In certain embodiments, the pharmaceutical composition is a controlled release pharmaceutical composition. For example, a controlled release pharmaceutical composition can be obtained by applying an enteric coating to an oral dosage form. In certain embodiments, the enteric coating comprises a film-forming agent, a plasticizer, and, optionally, an anti-sticking agent.

Suitable film-forming agents include agar, carbomer homopolymer and copolymers (i.e., high molecular weight, crosslinked, acrylic acid-based polymers), carboxymethyl cellulose, carboxymethylethyl cellulose, carrageen, cellulose acetate phthalate, cellulose acetate succinate, cellulose acetate trimelliate, chitin, corn protein extract, ethyl cellulose, gum arabic, hydroxypropyl cellulose, hydroxypropylmethyl acetate succinate, hydroxypropyl methylcellulose acetate succinate, hydroxypropyl methylcellulose phthalate, methacrylic acid-ethyl methacrylate-copolymer, methyl cellulose, pectin, polyvinyl acetate phthalate, polivinyl alcohol, shellac, sodium alginate, starch acetate phthalate and/or styrene/maleic acid copolymer or mixtures of said film-forming polymers. Cellulose acetate phthalate, hydroxypropyl methylcellulose acetate succinate and/or methacrylic acid-ethyl methacrylate-copolymer are the preferred film-forming agents. Most preferred is hydroxypropyl methylcellulose phthalate, such as HP 55 or HPMCP HP-50. Synthetic oils are not to be regarded as preferred film-forming agents. The foregoing list of film-forming agents is not meant to be exhaustive but merely illustrative, as a person or ordinary skill in the art would understand that many other film-forming agents or combination of film-forming agents could also be used.

The plasticizer(s) may generally be present in an amount greater than about 1.5%, and typically in an amount between about 2% and about 20% by weight, relative to the film-forming agent. The plasticizer may contain saturated linear monohydric alcohols having 12 to 30 carbon atoms. More specifically, acceptable plasticizers include lauryl alcohol, tridecyl alcohol, myristyl alcohol, pentadecyl alcohol, cetyl alcohol, heptadecyl alcohol, stearyl alcohol, nonadecyl alcohol, arachic alcohol, behenyl alcohol, camaubyl alcohol, ceryl alcohol, corianyl alcohol, melissyl alcohol, acetyl tributyl citrate, dibutyl sebacate, fatty acid esters of glycerol, glycerol, polyethylene glycol, propyleneglycol, sorbitan fatty acids, triacetin, triethyl citrate and mixtures of said plasticizers. Preferred plasticizers are cetyl alcohol, stearyl alcohol, triethyl citrate and mixtures thereof. When cetyl alcohol is used as a single plasticizer, it may be present in an amount of greater than about 1.5%, typically in an amount of about 2% to about 15%, preferably about 2% to about 10%, by weight relative to the film-forming agent. When triethyl citrate is used as a single plasticizer, it may be present in an amount between about 5% and about 20%, preferably between about 12% and about 15%, by weight relative to the film-forming agent. Synthetic oils and monomeric phthalic acid esters are not to be regarded as suitable plasticizers. The foregoing list of plasticizers is not meant to be exhaustive but merely illustrative, as a person or ordinary skill in the art would understand that many other plasticizers or combination of plasticizers could also be used so long as they are substantially free of both synthetic oils and monomeric phthalic acid esters.

In certain embodiments the plasticizer is comprised of cetyl alcohol and triethyl citrate which are collectively present in an amount of greater than about 3%, typically in an amount of about 4% to about 20%, in particular between about 6% and about 15%, more particularly between about 7% and about 10%, by weight in relation to the film-forming agent. The weight to weight ratio of cetyl alcohol to triethyl citrate when both are present may be from about 0.05:1 to about 1:1, for example 0.1:1, 0.2:1, 0.3:1, 0.4:1, 0.5:1, 0.6:1, 0.7:1, 0.8:1 or 0.9:1. In particular, the ratio of cetyl alcohol to triethyl citrate may be from about 0.25:1 to about 0.5:1, preferably from about 0.3:1 to about 0.45:1, more preferably from about 0.35:1 to about 0.4:1, and even more preferably from about 0.38:1 to about 0.4:1 (w/w).

The enteric coating optionally comprises an anti-sticking agent. Suitable anti-sticking agents include dimethicone and castor oil. Dimethicone, in particular dimethicone 1000, is the preferred anti-sticking agent. The amount of anti-sticking agent (if present) in the enteric coating is between about 1.5% and about 3% by weight relative to the film-forming agent. Synthetic oils are not to be regarded as preferred anti-sticking agents. The foregoing list of anti-sticking agents is not meant to be exhaustive but merely illustrative, as a person or ordinary skill in the art would understand that many other anti-sticking agents or combination of anti-sticking agents could also be used.

In certain embodiments the enteric coating comprises between about 5% and about 30% by weight, more preferably between about 7% and about 20% by weight, yet more preferably between about 10% and about 15% by weight of the total composition of the enteric coated oral dosage form or controlled release pharmaceutical composition. In certain embodiments the enteric coating comprises between about 20% and about 30% by weight, more preferably between about 22% and about 26% by weight, yet more preferably between about 22.5% and about 25% by weight of the total composition of the enteric coated oral dosage form or controlled release pharmaceutical composition.

In certain embodiments, the pharmaceutical composition is a controlled release capsule for oral administration. The capsule may contain enteric-coated pellets comprising lipase, protease, and amylase. The enteric-coated pellets may have a first dimension between about 0.5 mm and about 2.0 mm and, optionally, a second dimension between about 0.5 mm and about 2.0 mm. For example, the enteric-coated pellets may be approximately spherical and have a diameter from about 0.71 to about 1.60 mm. As another example, the enteric-coated pellets may be strand-like and have a diameter from about 0.5 mm and about 2.0 mm and a length from about 0.5 mm and about 2.0 mm. The composition may further include inactive ingredients described herein, such as cetyl alcohol, dimethicone, hypromellose phthalate, polyethylene glycol, and triethyl citrate.

In certain other embodiments, the pharmaceutical composition is an immediate release pharmaceutical composition. For example, the immediate release pharmaceutical composition may lack an enteric coating.

D. METHODS OF USE

In at least one aspect, the present invention includes a method of treating exocrine pancreatic insufficiency in a subject, in particular a human subject, in need of such treatment. The method comprises administering an enzyme preparation or a pharmaceutical composition containing an enzyme preparation to the subject. In certain embodiments, the exocrine pancreatic insufficiency is due to cystic fibrosis, chronic pancreatitis, pancreatectomy, or other conditions.

In another aspect, the present invention includes a method of treating or preventing maldigestion in a subject, in particular a human subject, in need of such treatment or prevention. In certain embodiments, the maldigestion is due to chronic exocrine pancreatic insufficiency, such as in subjects suffering from cystic fibrosis, chronic pancreatitis or patients who have undergone upper gastrointestinal surgery.

In another aspect, the present invention includes the use of an enzyme preparation or a pharmaceutical composition containing an enzyme preparation for treating exocrine pancreatic insufficiency in a subject in need of such treatment.

In another aspect, the present invention includes the use of an enzyme preparation or a pharmaceutical composition containing an enzyme preparation for the treatment or the prophylaxis of maldigestion in a subject in need of such treatment or prophylaxis.

In certain embodiments related to the methods and uses mentioned above, the enzyme preparation comprises pancreatin. In certain embodiments, a suitable dosage of pancreatin may be based on lipase units. The Cystic Fibrosis Foundation (CFF) has published Consensus Guidelines that contain recommended total daily doses of lipase units.

In certain embodiments, from 2,000 to 4,000 lipase units, preferably 3,000 lipase units, per 120 mL of formula or per breast-feeding is administered to an infant up to 12 months of age.

In certain embodiments, from 1,000 to 2,500 lipase units per kg of body weight per meal is administered to an individual from one (1) to four (4) years of age. In certain embodiments, from 500 to 2,500 lipase units per kg of body weight per meal is administered to an individual at least four (4) years of age.

In certain embodiments, the maximum daily dosage does not exceed 10,000 lipase units per kg of body weight. In certain embodiments, the maximum daily dosage does not exceed 4,000 lipase units per g of fat ingested.

In certain embodiments, the enzyme preparation or the pharmaceutical composition containing the enzyme preparation is administered immediately prior to a meal. In certain embodiments, the enzyme preparation or the pharmaceutical composition containing the enzyme preparation is administered during a meal or a snack.

In yet another embodiment, a method is provided for the treatment of a medical condition such as digestive disorders, pancreatic exocrine insufficiency, pancreatitis, cystic fibrosis, diabetes type I and/or diabetes type II by administering a therapeutically effective amount of an enzyme preparation or a pharmaceutical composition containing an enzyme preparation to a person in need of such treatment.

In at least one aspect, the present invention includes a method of digesting a protein. The method comprises contacting the protein to be digested with an enzyme preparation under conditions sufficient to digest the protein.

In certain embodiments, the enzyme preparation comprises one or more enzymes and/or proenzymes extracted from the electron beam irradiated animal tissue. In certain embodiments, the enzyme preparation comprises one or more enzymes isolated from the electron beam irradiated animal tissue. In certain embodiments, the enzyme preparation is in a crude form.

In certain embodiments, the step of contacting occurs in vivo. In certain embodiments, the step of contacting occurs in vitro.

In certain embodiments, the digested protein is used to prepare a protein hydrolysate product.

The enzyme preparations, compositions, methods, and uses described herein will be better understood by reference to the following exemplary embodiments and examples, which are included as an illustration of and not a limitation upon the scope of the invention.

E. EXEMPLARY EMBODIMENTS

One aspect of the present invention includes an enzyme preparation produced by a method comprising the steps of: (a) providing mammalian pancreatic tissue; (b) subjecting the pancreatic tissue to electron beam radiation to produce irradiated pancreatic tissue, wherein the electron beam radiation is sufficient to produce a reduction in microbial and/or viral load; and (c) isolating pancreatin from the irradiated pancreatic tissue. In certain embodiments, the isolating step comprises initiating hydrolysis or autolysis of the pancreatic tissue. In certain embodiments, the isolating step comprises mixing the irradiated pancreatic tissue with water. In certain embodiments, step (c) comprises activating a proenzyme from the irradiated pancreatic tissue. In certain embodiments, the reduction in microbial and/or viral load is at least a three $\log_{10}$, preferably at least a four $\log_{10}$, reduction relative to a control sample obtained from non-irradiated tissue. For example, the reduction in microbial and/or viral load is at least a three $\log_{10}$, preferably at least a four logo, reduction in PPV viral load relative to a control sample obtained from non-irradiated tissue. In certain embodiments, a biological activity of the enzyme preparation obtained in step (c) corresponds to at least 50%, preferably at least 90%, of the biological activity of a control enzyme preparation obtained from non-irradiated pancreatic tissue. In certain embodiments, the biological activity is lipase activity. In certain embodiments, the biological activity is protease activity or amylase activity. In certain embodiments, the method further comprises one or more additional steps that provide an additional reduction in microbial and/or viral load.

Another aspect of the present invention includes an enzyme preparation comprising one or more enzymes isolated from a mammalian tissue subjected to a treatment sufficient to produce at least a three $\log_{10}$, preferably at least a four $\log_{10}$, reduction in viral load. For example, the treatment is sufficient to produce at least a three $\log_{10}$, preferably at least a four $\log_{10}$, reduction in PPV viral load relative to a non-irradiated control sample.

Another aspect of the present invention includes an enzyme preparation comprising one or more enzymes isolated from mammalian tissue, wherein, prior to enzyme isolation, the mammalian tissue has been subjected to a treatment sufficient to produce at least a three $\log_{10}$, preferably at least a four $\log_{10}$, reduction in viral load. For example, the treatment is sufficient to produce is at least a three $\log_{10}$, preferably at least a four $\log_{10}$, reduction in PPV viral load relative to an untreated control sample. In certain embodiments, the mammalian tissue is a porcine pancreatic gland. In certain embodiments, the porcine pancreatic gland is flaked. In certain embodiments, the porcine pancreatic gland is in a frozen block. In certain embodiments, the porcine pancreatic gland is a whole gland or portion thereof, such as one or more lobes. In certain embodiments, the one or more enzymes comprise pancreatin. In certain embodiments, the treatment comprises electron beam radiation. In certain embodiments, the electron beam radiation has a dose from about 5 to about 50 kGy, preferably from about 10 to about 40 kGy. In certain embodiments, a biological activity of the enzyme preparation corresponds to at least 50%, preferably at least 90%, of the biological activity of a control enzyme preparation obtained from an untreated mammalian tissue. In certain embodiments, the biological activity is lipase activity. In certain embodiments, the biological activity is protease activity or amylase activity. In certain embodiments, the reduction in viral load is an orthogonal reduction.

Another aspect of the present invention includes a method for reducing the risk of contamination of a pancreatin product by an infectious agent comprising the steps of: (a) providing mammalian pancreatic tissue; (b) subjecting the pancreatic tissue to electron beam radiation to produce irradiated pancreatic tissue, wherein the electron beam radiation is sufficient to reduce the risk of contamination by an infectious agent; and (c) isolating pancreatin from the irradiated pancreatic tissue, thereby obtaining a pancreatin product with a reduced risk of contamination by the infectious agent relative to the mammalian pancreatic tissue provided in step (a) or a pancreatin sample derived from non-irradiated pancreatic tissue. In certain embodiments, the infectious agent is porcine parvovirus (PPV). In certain embodiments, the method provides at least a three $\log_{10}$, preferably at least a four $\log_{10}$, reduction in a measure indicative of a level or activity of a non-enveloped virus, such as porcine parvovirus (PPV). In certain embodiments, the measure indicative of the level or activity of the non-enveloped virus is viral load.

Another aspect of the present invention includes an enzyme preparation comprising one or more enzymes isolated from a mammalian tissue and a substantially inactivated non-enveloped virus, wherein the preparation has a biological activity that corresponds to at least 50%, preferably at least 90%, of the biological activity of a control preparation. In certain embodiments, the control preparation has not been subjected to a treatment sufficient to inactivate the non-enveloped virus. In certain embodiments, the substantially inactivated non-enveloped virus is porcine parvovirus (PPV). In certain embodiments, the one or more enzymes comprise pancreatin. In certain embodiments, the one or more enzymes are isolated from the mammalian tissue. In certain embodiments, the mammalian tissue is an electron beam irradiated mammalian tissue.

Another aspect of the present invention includes a pharmaceutical composition comprising one or more enzymes isolated from a mammalian tissue that has been has been subjected to a treatment to reduce risk of viral and microbial infectivity, wherein the composition has a biological activity that corresponds to at least 50%, preferably at least 90%, of the biological activity of a control composition. In certain embodiments, the one or more enzymes comprise a lipase. In certain embodiments, the control composition comprises an untreated sample of mammalian tissue corresponding to the mammalian tissue that has been subjected to a treatment to reduce risk of viral and microbial infectivity. In certain embodiments, the treatment comprises electron beam radiation. In certain embodiments, the electron beam radiation has a dose from about 5 to about 50 kGy, preferably from about 10 to about 40 kGy.

Another aspect of the present invention includes a method for producing a pancreatin product comprising the steps of: (a) providing a mammalian pancreatic tissue; (b) subjecting the pancreatic tissue to electron beam radiation to produce irradiated pancreatic tissue; and (c) isolating pancreatin from the irradiated pancreatic tissue to obtain the pancreatin product. In certain embodiments, a biological activity of the pancreatin product obtained in step (c) corresponds to at least 50%, preferably at least 90%, of the biological activity of a control pancreatin product. In certain embodiments, the control pancreatin product is obtained from non-irradiated pancreatic tissue. In certain embodiments, the electron beam radiation is sufficient to produce at least a three $\log_{10}$, preferably at least a four $\log_{10}$, reduction in viral load. For example, the treatment is sufficient to produce a reduction in viral load is at least a three $\log_{10}$, preferably at least a four $\log_{10}$, reduction in PPV viral load relative to a non-irradiated control sample. In certain embodiments, the electron beam radiation has a dosage from about 5 to about 50 kGy, preferably from about 10 to about 40 kGy. In certain embodiments, the biological activity is lipase activity. In certain embodiments, the biological activity is protease activity or amylase activity.

Another aspect of the present invention includes a method for digesting a protein comprising the steps of: (a) providing an enzyme or proenzyme preparation isolated from an electron beam irradiated animal tissue; and (b) contacting the protein with the enzyme or proenzyme preparation under conditions sufficient to digest the protein. In certain embodiments, the step of contacting occurs in vivo. In certain embodiments, the step of contacting occurs in vitro. In certain embodiments, the animal tissue is porcine pancreas. In certain embodiments, the digested protein is used to prepare a protein hydrolysate product. In certain embodiments, the enzyme or proenzyme preparation derived from an electron beam irradiated animal tissue exhibits at least a three $\log_{10}$, preferably at least a four $\log_{10}$, reduction in viral load compared to a control enzyme or proenzyme preparation derived from non-irradiated animal tissue. In certain embodiments, the enzyme or proenzyme preparation derived from an electron beam irradiated animal tissue exhibits a biological activity corresponding to at least 50%, preferably at least 90%, of the biological activity of a control enzyme or proenzyme preparation derived from non-irradiated animal tissue.

Another aspect of the present invention includes an enzyme preparation comprising one or more enzymes isolated from electron beam irradiated pancreatic tissue. In certain embodiments, the pancreatic tissue comprises a porcine pancreatic gland. In certain embodiments, the porcine pancreatic gland is frozen and mechanically processed into flakes or blocks prior to irradiation. Thus, in some such embodiments, the pancreatic tissue subject to electron beam irradiation is flaked frozen pancreatic tissue or a frozen block of pancreatic tissue. In certain embodiments, the porcine pancreatic gland is a whole gland or portion thereof, such as one or more lobes. In certain embodiments, the one or more enzymes comprise pancreatin. In certain embodiments, the enzyme preparation exhibits at least a three $\log_{10}$, preferably at least a four $\log_{10}$, reduction in viral load compared to a control enzyme preparation. For example, the enzyme preparation exhibits at least a three $\log_{10}$, preferably at least a four $\log_{10}$, reduction in PPV viral load relative to a control enzyme preparation. In certain embodiments, a biological activity of the enzyme preparation corresponds to at least 50%, preferably at least 90%, of the biological activity of a control enzyme preparation. In certain embodiments, the biological activity is lipase activity. In certain embodiments, the biological activity is protease activity or amylase activity. In certain embodiments, the control enzyme preparation is obtained from non-irradiated tissue. In certain embodiments, the reduction in viral load is an orthogonal reduction.

Another aspect of the present invention includes a method of treating exocrine pancreatic insufficiency, comprising: administering a dose of any of the foregoing enzyme preparations and/or pharmaceutical compositions to a subject in need thereof. In certain embodiments, the exocrine pancreatic insufficiency is due to cystic fibrosis or chronic pancreatitis.

F. EXAMPLES

Example 1. E-Beam Irradiation of Porcine Parvovirus (PPV), Pancreatin API, and Porcine Pancreas Materials and Methods.

Vialed Porcine Parvovirus in Cell Culture Fluid.

Because the porcine gland tissue itself may have some inactivating effects on viruses, initially, the virus samples used for these studies were prepared from infected cell cultures. Porcine Parvovirus (PPV), Strain NADL-2 (ATCC® VR-742™) and Pig Testis (ST) cells (ATCC® CRL-1746™) were purchased from American Type Culture Collection (ATCC). PPV was propagated, cultured and maintained according to ATCC recommendations. PPV was propagated to an approximate titer of $10^8$ virus Infectious Units (IU)/ml. Virus was harvested from lysed cells in cell culture media consisting of Minimum Essential Medium (MEM), 10% Fetal Bovine Serum (FBS), 2 mM Glutamine, 100 units/ml penicillin, 100 mg/ml streptomycin.

PPV was packaged in vials and then double bagged prior to shipment. The vials were Nalgene Cryogenic Vials (i.e., polypropylene with externally threaded high density polyethylene (HDPE) closure with a leak-proof sealing ring having a length of 1.87 in; a diameter of 0.5 in.; a capacity of 2.0 ml; and fill volume of 1.0 ml. Each individual vial was placed in a Food Saver bag (polyethylene with an outer layer of nylon) and vacuum sealed. The bags were trimmed to just fit the vial. Four individually sealed vials were then placed inside another Food Saver bag (approximately 11×14") and vacuum sealed.

Frozen Flaked Porcine Pancreas Glands.

Pancreas glands obtained from butcher hog (Animal Technologies, Tyler, Tex.) were kept on dry ice.

Frozen flaked porcine pancreas glands were placed in a 12"×12"×1¾" container (clear polypropylene), which was vacuumed sealed inside a clear 3 mil poly/nylon bag. The bag was heat sealed. The pancreas glands were held on dry-ice to ensure temperatures below –20° C. The sample weight of the frozen flaked porcine pancreas gland was 1.05 kg plus a packaging weight of 270 grams (0.27 kg). The lid weighed 100 g. The surface density was 1.3 g/cm². Two packages were made for each radiation dose including control without radiation, one intact package was used for isolation of the enzyme preparation after transit back to the site where the isolation was conducted with the other package being a reserve.

Pancreatin (API).

Two types of pancreatin API were used: Pancreatin N and Pancreatin S. Both API were held at ambient conditions. Pancreatin N (Material #1030828, Abbott Laboratories) is a light yellow/gray to off-white powder. Pancreatin N originated from butcher hog pancreas. Pancreatin S (Material #1030829, Abbott Laboratories) is a light yellow/gray to off-white powder. Pancreatin S originated from sow pancreas.

Pancreatin API was placed in a 2½"×3½"×1⅝%" container (clear polypropylene), which was vacuumed sealed inside a clear 3 mil poly/nylon bag. The bag was heat sealed. The sample weight of the pancreatin API was 80 grams plus a packaging weight of 26 grams. The surface density was 1.4 g/cm². Samples of Pancreatin N were exposed to electron beam radiation at the indicated dose. The control was not exposed to electron beam radiation. Pancreatin N was assayed for activity after transit back to the experimental site. Pancreatin N was derived from butcher hog. All Pancreatin N packages arrived intact from the irradiation site.

E-Beam Irradiation.

The source of the electron beam was an Industrial Materials Processing Electron Linear Accelerator (IMPELA®; Iotron Industries, Inc. Columbia City, Ind.), 10 MeV, 80 cm scan width.

The samples of packaged frozen flaked porcine pancreas and porcine parvovirus were held below –20° C. by placing on dry ice contained in an aluminum tray. Dosimeters were placed on the upper surface of each sample. The samples of packaged pancreatin API maintained at ambient temperature were placed on an expanded polystyrene foam sheet, dosimeters were placed on the upper surface. The packages were sent on a conveyor belt under the E Beam scan horn. After one pass of radiation, the dosimeters were retrieved. The packages were sent below the radiation horn for a second pass after inverting the package (upper side is now facing down) and a new dosimeter was placed on the upper surface. After the second round of radiation, the packages and dosimeters were retrieved. The frozen flaked porcine pancreas and porcine parvovirus packages were retrieved and placed on dry ice for shipment. The packages of pancreatin API were retrieved and held at ambient temperature for shipment. The control packages of frozen flaked pancreas and porcine parvovirus placed on dry ice were prepared for re-shipment on dry ice without undergoing radiation. The control packages of pancreatin API held at ambient temperature were prepared for re-shipment at ambient without undergoing radiation. The electron beam dosage was calculated from the dosimeter exposure using a calibration curve.

Viral Infectivity Testing.

Viral infectivity was determined by titration of ten-fold dilutions in 96 well microplates using appropriate controls for triplicate samples at each energy dose. The virus titers were calculated using the Reed and Muench method described in Reed, L. J.; Muench, H. (1938). "A simple method of estimating fifty percent endpoints." The American Journal of Hygiene 27: 493-497 and expressed as a 50% $TCID_{50}$ per mL.

Pancreatin Isolation and Testing.

The method used for isolation of pancreatin is substantially similar to that described in U.S. Pat. No. 4,623,624 that comprises hydrolysis and/or autolysis, followed by fiber sieving, precipitation of enzymes, separation of precipitate by filtration and/or centrifugation, washing of the cake, drying and particle size reduction. Hydrolysis was performed using one package corresponding to each radiation dosage including the unirradiated control. A package without damage to the packaging (such as large cracks) was selected for each isolation experiment. Due to the care taken during transit back to the experimental site, all packages arrived intact and one package was selected at random for each radiation dosage including control for isolation. Pancreatin from an earlier isolation was used as a protease source to start the hydrolysis. Calcium hydroxide was used to supply calcium ions needed for activation of the proteases. Sodium bicarbonate is used as a buffering agent for the hydrolysis. Simethicone was used as an antifoam agent. The hydrolysis of the pancreas was performed close to ambient temperature. The completion of hydrolysis was checked by centrifugation of the hydrolyzed mixture after addition of isopropanol as described below. After completion of hydrolysis additional isopropanol was added to reduce the hydrolysis rate, the mixture was cooled, the mixture was stirred and fibers were separated using a 0.425 inch mesh. The fibers were washed with isopropanol and compressed to expel the liquid that is held. The wash was combined with the filtrate obtained earlier. Additional isopropanol was added to the filtrate to cause precipitation of the enzymes. The suspension was filtered through filter cloth with 15 micron openings and washed with increasing concentrations of isopropanol with isopropanol absolute as the final wash. The cake was dried on the filter cloth under nitrogen flow while pulling vacuum below the filter cloth till the cake appeared dry visually (color of cake turns lighter after removal of isopropanol and water). The cake was peeled away from the filter cloth and dried under vacuum and nitrogen flow at temperature below about 50° C. to a water content by Karl Fischer of 3.5% or lower. The yield of dry pancreatin is 80 to 100 g from 1 Kg of frozen flaked porcine pancreas from butcher hog.

Centrifugation Test for Completion of Hydrolysis.

Sample three scoops of about 10 ml from the hydrolysis vessel and pass through 0.425 mm sieve, collect filtrate into plastic beaker (scrape filtrate into plastic beaker also), discard the fibers that are retained on the mesh. Using a pipette, add 10 g solution from reactor to 50 mL centrifuge tube, add 5.5 mL IPA 85%, stir for 1 minute with spatula. Add 20 mL IPA 85% to filtrate in 50 mL centrifuge tube. Stir for one minute with spatula. Centrifuge suspension at approximately 90×g for two minutes.

The first sample may be taken two hours after start of hydrolysis or when color is changing from pink to brownish and suspension becomes thinner (about 2 hours).

The next sample is taken when color is brown without pink shade, at this point sediment is expected to be about 25%, the sediment will be less firm and stragglers may be present in clear layer above. After this, sampling may be done at every half an hour intervals as possible.

Hydrolysis stopped if two subsequent measurements show less than 20% of sediments. At this point sediment will be firm and without stragglers in clear layer above.

Two-sided electron beam irradiation of vialed PPV was performed in triplicate. Data for viral load reduction and log kill of PPV exposed to electron beam radiation are shown in Table 1:

TABLE 1

| Dosage (KGy) | 0 | 9.5 | 19.25 | 38.45 | 0 | 9.5 | 19.25 | 38.45 |
|---|---|---|---|---|---|---|---|---|
| | Viral Load Virus titer/mL | Viral Load Virus titer/mL | Viral Load Virus titer/mL | Viral Load Virus titer/mL | Log Kill | Log Kill | Log Kill | Log Kill |
| Test A | 1.50E+08 | 2.50E+06 | 1.50E+05 | | 0.00E+00 | 1.78E+00 | 3.00E+00 | |
| Test B | 1.50E+08 | 6.34E+06 | 6.34E+04 | | 0 | 1.37E+00 | 3.37E+00 | |
| Test C | 4.00E+08 | 1.26E+06 | 4.00E+05 | 1.50E+02 | 0 | 2.50E+00 | 3.00E+00 | 6.43E+00 |
| Mean | | | | | 0 | 1.88E+00 | 3.12E+00 | 6.43E+00 |

E-beam dosage was determined by estimating the dose absorbed by each sample from the surface dose as indicated by the dosimeter affixed to the sample container.

Table 1 shows that exposure of PPV to about 40 kGy provides about a 6.5 $\log_{10}$ kill, while exposure to about 20 kGy provides about a 3 $\log_{10}$ kill. Based on these data, it is expected that exposure to about 30 kGy will provide at least a 4 $\log_{10}$ kill.

Exposure of PPV to about 60 kGy, about 80 kGy, or about 100 kGy resulted in final viral titers below the limit of detection of the assay.

Pancreatin was tested for free protease, amylase, and lipase activity as described in USP by validated methods. Pancreatin was tested for total protease as described in European Pharmacopoeia (EP) by validated methods.

Two-sided electron beam irradiation of Pancreatin N was performed. All the Pancreatin N containers were received intact at the experimental site and were used for assay. The Data for enzymatic activity of pancreatin API exposed to electron beam radiation are shown in Table 2:

| E Beam Dose KGy | Lipase Activity USP Units/gram | Amylase Activity USP Units/gram | Total Protease Activity USP Units/gram | Free Protease Activity USP Units/gram |
|---|---|---|---|---|
| Control (0 kGy) | 89106 | 564390 | 383192 | 314093 |
| 18.6 kGy | 63328 | 398752 | 321567 | 266540 |
| 37.45 kGy | 58631 | 386628 | 302341 | 244531 |
| 56.5 kGy | 47755 | 282378 | 272499 | 232087 |
| 76.35 kGy | 40583 | 272760 | 259117 | 214914 |
| 99.4 kGy | 37799 | 286652 | 247005 | 196356 |

Table 2 shows that exposure of pancreatin API to about 20 kGy provides about a 30% loss in lipase activity, exposure of pancreatin API to about 40 kGy provides about a 35% loss in lipase activity, exposure of pancreatin API to about 60 kGy provides about a 46% loss in lipase activity, exposure of pancreatin API to about 80 kGy provides about a 54% loss in lipase activity, and exposure of pancreatin API to about 100 kGy provides about a 58% loss in lipase activity. Based on these data, it is expected that exposure of pancreatin API to about 30 kGy will provide at least a 30% loss in lipase activity.

Two-sided electron beam irradiation of butcher hog pancreas was performed. Data for enzymatic activity of pancreatin derived from frozen flaked porcine pancreas gland exposed to electron beam radiation are shown in Table 3:

| E Beam Dose KGy | Lipase Activity USP Units/gram | Amylase Activity USP Units/gram | Total Protease Activity USP Units/gram | Free Protease Activity USP Units/gram |
|---|---|---|---|---|
| Control (0 kGy) | 74986 | 423487 | 243421 | 151365 |
| 18.75 kGy | 74741 | 449569 | 337594 | 128749 |
| 35.5 kGy | 65348 | 349816 | 360407 | 128506 |
| 56.55 kGy | 57976 | 398281 | 268297 | 119727 |
| 77.4 kGy | 34806 | 251691 | 175994 | 109158 |
| 100.4 kGy | 36362 | 276118 | 206217 | 100342 |

Table 3 shows that exposure of frozen flaked porcine pancreas glands to about 20 kGy provides about a 1% loss in lipase activity, exposure of frozen flaked porcine pancreas glands to about 40 kGy provides about a 13% loss in lipase activity, exposure of frozen flaked porcine pancreas glands to about 60 kGy provides about a 23% loss in lipase activity, exposure of frozen flaked porcine pancreas glands to about 80 kGy provides about a 54% loss in lipase activity, and exposure of frozen flaked porcine pancreas glands to about 100 kGy provides about a 52% loss in lipase activity. Based on these data, it is expected that exposure of frozen flaked porcine pancreas glands to about 30 kGy will provide about a 10% loss in lipase activity.

As shown in Tables 2 and 3, electron beam irradiation of the pancreatin API produces more loss of enzyme activity as compared to electron beam irradiation of the pancreatic tissue prior to isolation. Without wishing to be bound by theory, the resistance of the intact tissue to electron beam irradiation may be due to the conformation of the enzyme (e.g., as a proenzyme) in the source tissue and/or co-factors in the source tissue providing structural protection.

Example 2. E-Beam Irradiation of Whole Porcine Pancreas Glands

A further study was performed using whole porcine pancreas. Approximately 3.6 kg thawed porcine pancreas was packed into wax lined cardboard boxes that were approximately 10×15×1.5 inches thick. The boxes were frozen to −20° C. and held until use for e-beam irradiation. Boxes were shipped for e-beam irradiation by frozen truck (−20° C.). Boxes were removed from the frozen truck and then exposed to double-sided electron beam irradiation— unirradiated boxes served as a control. Five (5) boxes were used for each nominal radiation dose: 0, 15, 20, and 25 kGy and shipped back for evaluations by frozen truck (−20° C.), including the unirradiated boxes, and then held at −20° C.

Frozen pancreas samples were selected from each box at random locations within the box for subsequent isolation of pancreatin. Isolation was performed as described herein. Pancreatin isolated from electron beam irradiated whole pancreas was then tested for enzyme activity according to a colorimetric assay.

Pancreatin samples (API) were tested using colorimetric kinetic analysis by a microplate reader with the use of substrates structurally similar to those used in USP 39 <Pancrelipase>. The enzyme activities were determined by measuring the production rate of the product relative to the pancrelipase reference standard. Analytical comparability has been demonstrated between the filed USP monograph methods and the alternate microplate reader methods.

The sampling, isolating and assaying procedure was repeated four times for each dose to obtain a total of five measurements for each dose. Mean values of five measurements are reported in Table 4.

TABLE 4

API Enzyme Activity after Irradiation of Whole Pancreas Glands

| E Beam Dose* KGy | Mean Lipase Activity USP Units/mg | Mean Amylase Activity USP Units/mg | Mean Free Protease Activity USP Units/mg | Mean Total Protease Activity USP Units/mg |
|---|---|---|---|---|
| Control (0 kGy) | 104 | 456 | 197 | 344 |
| 14.9 kGy | 99 | 435 | 201 | 291 |
| 19.9 kGy | 106 | 411 | 200 | 316 |
| 24.9 kGy | 104 | 395 | 183 | 301 |

*(minimum dose + maximum dose)/2

Table 4 shows that pancreatin isolated from a whole pancreas gland exposed to a dose of up to about 25 kGy electron beam irradiation has the same or substantially the same lipase activity as pancreatin isolated from a unirradiated control.

Example 3. Low Dose E-Beam Irradiation of Intact Porcine Pancreas Tissue

Further studies have been performed by spiking porcine pancreas tissue with live virus and then subjecting the virus-spiked tissue to electron beam radiation at lower dose (about 12.3 kGy) to enable virus recovery and assessment. This additional work was done to demonstrate effective inactivation of several related viruses at a low dose which would enable the effective enumeration of the impact of E-beam irradiation.

Selected viruses were deliberately spiked onto the tissue sample and the degree of virus clearance was evaluated by comparison of the amount of virus input to the amount of virus remaining after e-beam treatment. The viruses selected for this study are identified in Table 5.

TABLE 5

Viruses selected for viral clearance study

| Virus | Family | Genome | Envelope | Size (nm) | Physico-chemical resistance |
|---|---|---|---|---|---|
| Reovirus Type 3 (REO3) | Reo | RNA | No | 60-80 | Medium |
| Porcine Parvovirus (PPV) | Parvo | DNA | No | 18-24 | High |
| Feline Calicivirus (FCV) | Calici | RNA | No | 35-39 | Medium |

REO3 has a double-stranded RNA, segmented genome and belongs to the Reoviridae Family of viruses, which also includes rotavirus. Thus, REO 3 can serve as a model for rotavirus. FCV has been used as a model viruses for the validation of inactivation methods in blood products and, in particular, as a model for hepatitis E virus (HEV).

Porcine pancreas glands were sliced and ground. The tissue was then added to a petri dish, and spiked with the indicated virus. Standard virus stocks had certified titers of at least $1 \times 10^7$ pfu/mL. The spiked sample was incubated at room temperature for a minimum of 60 minutes (until the tissue returned to its original dryness). Following the incubation, additional porcine pancreas tissue was added to the dish. The dish was sealed and placed on dry ice for shipment to the e-beam facility. Each dish contained approximately 13 grams of tissue and the density of the tissue was similar to the density of a whole gland.

For each virus, spiked recovery samples (unshipped) and an unirradiated shipping control (shipped to ebeam facility but not irradiated) were included.

Electron beam irradiation was performed at the ebeam facility. After exposure to electron beam radiation was complete, the irradiated samples and the unirradiated shipping controls were shipped back for evaluation of viral load. Upon receipt, the samples were stored at ≤−60° C. until testing.

For each sample, 50 mL of culture media was added to a sterile bottle. The tissue was extracted by performing 3 rounds of soaking for approximately 5-10 minutes at room temperature followed by a 15-30 second vortex. The samples were then centrifuged at 3,000 RPM for 10 minutes. The supernatant from the extraction was used for viral testing.

Virus titers were determined by standard plaque assays. The indicator cell type for REO3, PPV, and FCV were Vero, PT-1, and CRFK, respectively. Virus titers and viral clearance factors were calculated according to standard procedures. The virus clearance factor (VCF) was calculated as follows:

$$VCF = \log_{10}\left[\frac{\text{Volume} * \text{titer before processing}}{\text{Volume} * \text{titer after processing}}\right]$$

Data for viral clearance produced by exposure of spiked tissue to electron beam radiation are shown in Table 6.

TABLE 6

Viral Clearance after Irradiation of Pancreas Glands Spiked with Virus

| Model Virus | Log Total Virus | | VCF | 95% Confidence Limit |
|---|---|---|---|---|
| | Before Processing | After Processing | | |
| REO3 | 6.5 | <2.4 | ≥4.1 | 0.08 |
| FCV | 6.7 | 4.9 | 1.8 | 0.05 |
| PPV | 5.8 | 3.6 | 2.2 | 0.29 |

These studies confirmed that sufficient inactivation of viruses, including feline calicivirus (FCV) and reovirus 3 (REO3), could be achieved with electron beam radiation of an intact tissue. Moreover, irradiation of a pancreas gland followed by isolation of an enzyme preparation (e.g., pancreatin API) from the irradiated gland showed similar results with respect to loss in enzyme activity relative to a non-irradiated control to those shown in Table 3 where flaked porcine pancreas was used.

Example 4. E-Beam Irradiation of Minced Tissue and Homogenized Tissue

Minced pancreas: Frozen porcine pancreas glands were ground in a mincer and subsequently frozen for irradiation as described herein.

Homogenized pancreas: frozen porcine pancreas glands were ground in a mincer as described above and stirred in water at a temperature of 10° ° C.±5° C. until homogeneously mixed (about 75 min.). Samples were subsequently frozen for irradiation as described herein.

As a control end-product, pancreatin was used as a powder in therapeutic grade, according to the specification of Ph. Eur. Pancreatin powder was obtained directly from the manufacturer (Abbott Laboratories GmbH, Neustadt, Germany) and sampled from the manufacturing. Pancreatin for therapeutic use (according to Ph. Eur.) is also commercially available, e.g., from Nordmark, Uetersen, Germany, or BIOZYM Gesellschaft für Enzymtechnologie mbH, Hamburg, Germany, and/or can be produced according to known methods (see e.g. EP-A2 115023).

For the irradiation treatment, samples were removed from the freezer or refrigerator and placed on cooling accumulators to maintain temperature as described below. Temperature range was monitored and, if necessary, additional cooling steps were performed. Because the use of a thermometer is not possible with frozen samples, a thermal imaging camera (Testo 880-3, Testo AG Lenzkirch, Germany) was used where necessary to determine surface temperatures.

Homogenized pancreas tissue samples were thawed and irradiated at temperatures above 0° C. (T>0° C.) but below 20° C. The pancreatin samples were taken from the refrigerator and irradiated at T>0° C.

Samples were exposed to E-beam radiation using a Rhodotron TT-100 10 MeV, 35 kW electron beam accelerator (IBA Industrial, Louvain-La-Neuve, Belgium). The irradiation process was accomplished stepwise. Sample boxes passed the accelerator in 5 or 10 kGy steps until the required dose was achieved. For example, samples planned for lower doses were removed at the earlier steps and samples planned for the higher doses were re-exposed and irradiated again.

Enzymatic activities (i.e., lipolytic proteolytic, amylolytic activities) of the test samples before irradiation ("pre-treatment samples") were determined according to Ph. Eur.

relative to the relevant reference standards and taken as the initial enzymatic (lipolytic, proteolytic, amylolytic, as applicable) activities before irradiation treatment. Subsequently, test samples were irradiated as described herein. The enzymatic activities of the test samples after irradiation were determined ("post-treatment samples") in the same manner as for the pre-treatment samples. Retained enzyme activities in the post-treatment samples were determined and are reported as the relative percentage of the same enzyme activity determined in the pre-treatment sample.

Lipase activity was determined as follows as described in Ph. Eur: the required amount of the test sample (depending on the activity expected, approximately 2.5 g) was comminuted (e.g., crushed or ground, depending on state/consistency of test sample) and directly extracted with buffer solution. The hydrolytic activity of the lipase is determined with olive oil emulsion as substrate. The free fatty acids cleaved from the triglycerides of the olive oil are titrated with sodium hydroxide solution at a constant pH of 9.0. The lipase activity of the sample is determined by comparing the rate at which a suspension of the sample hydrolyses a substrate of olive oil emulsion with the rate at which a suspension of a standard pancreas reference powder (reference standard of Ph. Eur. as described in the monograph, "pancreas powder (lipase) BRP") hydrolyses the same substrate under the same conditions.

Lipase activity loss values are reported in Table 7.

TABLE 7

Enzyme Activity after Irradiation of Minced Tissue & Tissue Homogenate

| | Lipase Activity Loss (%) | | |
|---|---|---|---|
| E Beam Dose (kGy) | Pancreatin (end-product) | Minced pancreas tissue | Tissue homogenate |
| 10 | 24.0 | nt | 7.8 |
| 15 | 30.3 | 13.1 | 11.3 |
| 20 | 35.0 | 10.9 | 11.4 |
| 25 | nt | 19.8 | nt |
| 30 | 42.5 | 18.5 | 16.9 |
| 40 | 48.9 | nt | 24.3 |
| 50 | 53.6 | nt | 29.7 |

"nt": not tested

Irradiation of minced tissue or tissue homogenate (i.e., prior to chemical or enzymatic processing of the pro-enzyme population to active form) consistently resulted in improved enzyme activity retention relative to irradiation of end product. Irradiation of between 20 and 30 kGy resulted in activity losses of less than 20%, lower than that achieved by standard protocols.

Example 5. E-Beam Irradiation of Minced Tissue Spiked with *B. cereus*

Pancreas frozen after mincing was thawed, packed into sterile 50-×9-mm, polystyrene Petri dishes (Ted Pella, Inc., Redding, Calif., item 14014), spiked with approx. $10^8$ cfu of *B. cereus* endospores from a commercial pre-titered suspension (*B. cereus* ATCC 14579, Mesa Labs, Bozeman, Mont.), sealed in a vacuum ("seal-a-meal") bag and then frozen.

A range of E-beam dosage levels from 0 to 20 kGy in 5-kGy increments was selected in the present experiment with minced pancreas. Bags were shipped for e-beam irradiation on dry ice. Bags were exposed to electron beam irradiation—unshipped bags and unirradiated bags served as controls.

Samples will be returned on dry ice. All samples will then be diluted and plated on Trypticase Soy Agar plates (Biomerieux item M1040) for cfu enumeration. Plates will be incubated at 30-35° C. for 1-2 days until colonies are of countable size. CFU counts will be recorded.

The introduction of a decontamination step prior to processing the porcine pancreas provides effective control of known infectious agents both in terms of operator safety during the isolation of enzymes as well as patient safety. Thus, the use of an electron beam treatment that is effective to inactivate a wide spectrum of microbes and viruses, including difficult-to-inactivate viruses (e.g., porcine parvo virus) and spore-forming bacteria, with minimal loss in enzyme activity is advantageous over other methods.

As used herein, the electron beam radiation step can be considered an orthogonal viral inactivation step. The reduction in microbial and/or viral load obtained in the electron beam irradiated pancreatic tissue transfers to the pancreatin that is isolated from it in an additive manner with respect to the reduction obtained by other steps for microbial and/or viral reduction. Total $\log_{10}$ kill achieved by all the steps, including electron beam radiation, is the cumulative $\log_{10}$ kill achieved by all microbial and/or viral inactivation steps performed on the pancreatic tissue.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. An enzyme preparation produced by a method comprising the steps of:

(a) subjecting intact mammalian pancreatic tissue to electron beam radiation to produce irradiated pancreatic tissue, wherein the electron beam radiation is sufficient to produce at least a four $\log_{10}$ reduction in viral load of a model virus compared to a control sample; and (b) isolating pancreatin from the irradiated pancreatic tissue, wherein a biological activity of the pancreatin obtained in step (b) corresponds to at least 50% of the biological activity of a control enzyme preparation.

2. The enzyme preparation of claim 1, wherein the model virus is porcine parvovirus (PPV).

3. The enzyme preparation of claim 1, wherein the intact mammalian pancreatic tissue is flaked tissue, a whole gland, or a portion of a whole gland.

4. The enzyme preparation of claim 1, wherein step (b) comprises initiating hydrolysis or autolysis of the irradiated pancreatic tissue or activating a proenzyme from the irradiated pancreatic tissue.

5. The enzyme preparation of claim 1, wherein a biological activity of the enzyme preparation obtained in step (b) corresponds to at least 80% of the biological activity of a control enzyme preparation.

6. The enzyme preparation of claim 5, wherein the biological activity is lipase activity.

7. The enzyme preparation of claim 1, wherein the electron beam radiation has a dosage from about 5 to about 50 kGy.

8. An enzyme preparation comprising one or more enzymes isolated from an electron beam irradiated, intact pancreatic tissue, wherein a biological activity of the enzyme preparation corresponds to at least 90% of the biological activity of a control enzyme preparation.

9. The enzyme preparation of claim 8, wherein the electron beam irradiated, intact pancreatic tissue is flaked pancreatic tissue, a whole pancreas gland, or a portion of a whole pancreas gland.

10. The enzyme preparation of claim 8, wherein the one or more enzymes comprise pancreatin.

11. The enzyme preparation of claim 8, wherein the biological activity is lipase activity.

12. A pharmaceutical composition comprising the enzyme preparation of claim 1.

13. A method of treating exocrine pancreatic insufficiency, comprising:
    administering a dose of the enzyme preparation of claim 1 to a subject in need thereof.

14. The method of claim 13, wherein the exocrine pancreatic insufficiency is due to cystic fibrosis or chronic pancreatitis.

15. The enzyme preparation of claim 1, wherein the intact mammalian pancreatic tissue is chemically unprocessed prior electron beam radiation.

16. The enzyme preparation of claim 1, wherein step (a) is performed in an environment substantially free of flammable solvents.

17. A pancreatin product produced by a method comprising the steps of:
    (a) mechanically processing a frozen, intact pancreas gland or intact lobe thereof to obtain frozen blocks or flakes;
    (b) irradiating the frozen blocks or flakes in a container at a dose sufficient to produce at least a four $\log_{10}$ reduction in viral load of a model virus compared to a control sample, wherein the container is substantially free of flammable solvent; and
    (c) processing the irradiated blocks or flakes to obtain pancreatin;
    wherein a biological activity of the pancreatin corresponds to at least 90% of the biological activity of a control enzyme preparation.

18. The pancreatin product of claim 17, wherein step (b) comprises electron beam irradiation.

19. The pancreatin product of claim 18, wherein the electron beam radiation has a dosage from about 10 to about 40 kGy.

20. The pancreatin product of claim 17, wherein a biological activity of the pancreatin obtained in step (c) corresponds to at least 90% of the biological activity of a control enzyme preparation.

21. The pancreatin product of claim 20, wherein the biological activity is lipase activity.

22. The pancreatin product of claim 17, wherein the model virus is reovirus type 3 (REO3), feline calicivirus (FCV), or porcine parvovirus (PPV).

23. The pancreatin product of claim 17, wherein the model virus is porcine parvovirus (PPV).

24. The enzyme preparation of claim 1, wherein the model virus is reovirus type 3 (REO3), feline calicivirus (FCV), or porcine parvovirus (PPV).

25. The enzyme preparation of claim 8, further comprising a substantially inactivated non-enveloped virus.

26. The enzyme preparation of claim 25, wherein the substantially inactivated non-enveloped virus is porcine parvovirus (PPV).

27. A pancreatin product produced by a method comprising the steps of:
    (a) mechanically processing a frozen, intact pancreas gland or intact lobe thereof to obtain frozen blocks or flakes;
    (b) subjecting the frozen blocks or flakes to electron beam irradiation at a dose sufficient to produce at least a four $\log_{10}$ reduction in viral load of a model virus compared to a control sample, wherein the frozen blocks or flakes are irradiated in a container that is substantially free of flammable solvent; and
    (c) processing the irradiated blocks or flakes to obtain pancreatin;
    wherein a biological activity of the pancreatin corresponds to at least 90% of the biological activity of a control enzyme preparation.

28. The pancreatin product of claim 27, wherein the electron beam radiation has a dosage from about 10 to about 40 kGy.

29. The pancreatin product of claim 27, wherein the biological activity is lipase activity.

30. The pancreatin product of claim 27, wherein the model virus is reovirus type 3 (REO3), feline calicivirus (FCV), or porcine parvovirus (PPV).

31. The pancreatin product of claim 27, wherein the model virus is porcine parvovirus (PPV).

32. The pancreatin product of claim 27, wherein the method further comprises, following step (b), testing for the presence or amount of a viral contaminant in a sample derived from the irradiated blocks or flakes.

33. The pancreatin product of claim 27, wherein the viral contaminant arises from a Reoviridae virus, a Parvoviridae virus, or a Caliciviridae virus.

34. A pharmaceutical composition comprising the pancreatin product of claim 27.

35. A method of treating exocrine pancreatic insufficiency, comprising:
    administering a dose of the pancreatin product of claim 27 to a subject in need thereof.

\* \* \* \* \*